(12) United States Patent
Johnson et al.

(10) Patent No.: US 7,722,588 B1
(45) Date of Patent: May 25, 2010

(54) MULTILAYERED APERTURED FILM WRAPPING ELEMENT FOR ABSORBENT ARTICLES

(75) Inventors: Bruce C. Johnson, Whiting, NJ (US); Judith Roller, North Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/345,090

(22) Filed: Jun. 30, 1999

(51) Int. Cl.
*A61F 13/15* (2006.01)

(52) U.S. Cl. .................. 604/385.18; 604/904; 604/378; 604/383

(58) Field of Classification Search .................. 604/378, 604/383, 385.18, 904; 428/131, 132, 137, 428/174, 172, 411.1
See application file for complete search history.

(56) References Cited

U.S. PATENT DOCUMENTS

| | | |
|---|---|---|
| 3,054,148 A | 9/1962 | Zimmerli |
| 4,100,324 A | 7/1978 | Anderson et al. |
| 4,690,679 A | 9/1987 | Mattingly et al. |
| 4,695,422 A | 9/1987 | Curro et al. |
| 4,710,186 A | 12/1987 | DeRossett et al. |
| 4,741,877 A | 5/1988 | Mullane, Jr. |
| 4,816,100 A | 3/1989 | Friese |
| 4,859,273 A | 8/1989 | Friese |
| 4,863,450 A | 9/1989 | Friese |
| 4,876,156 A | 10/1989 | Hwo |
| 5,115,030 A | 5/1992 | Tanaka et al. |
| 5,294,482 A | 3/1994 | Gessner |
| 5,342,334 A | 8/1994 | Thompson et al. |
| 5,403,300 A | 4/1995 | Howarth |
| 5,567,376 A | 10/1996 | Turi et al. |
| 5,804,286 A | 9/1998 | Quantrille et al. |
| 5,916,462 A | 6/1999 | James et al. |
| 6,228,462 B1 * | 5/2001 | Lee et al. ..................... 428/132 |

FOREIGN PATENT DOCUMENTS

| | | |
|---|---|---|
| EP | 0230113 | 7/1987 |
| EP | 0394954 A | 10/1990 |
| EP | 0422660 | 4/1991 |
| EP | 0844280 | 5/1998 |
| EP | 0924328 A | 6/1999 |
| WO | WO 9745259 A | 12/1997 |
| WO | WO 9900096 A | 1/1999 |

OTHER PUBLICATIONS

U.S. Appl. No. 09/343,759.
U.S. Appl. No. 09/345,088.
U.S. Appl. No. 09/345,089.
U.S. Appl. No. 09/343,760.
U.S. Appl. No. 60/141,688.
U.S. Appl. No. 60/141,690.
International Search Report, PCT/US00/13395, dated Sep. 5, 2000.

* cited by examiner

*Primary Examiner*—Dennis Ruhl

(57) ABSTRACT

A multilayered apertured film wrapping element for an absorbent article is disclosed. At least one outer layer of the fluid-impervious plastic material has a continuous phase of a thermoplastic polymeric component and an immiscible, dispersed phase of a thermoplastic polymeric component having a lower melting point. The wrapping element is useful in applications involving heat sealing and similar thermal processes in absorbent articles, such as sanitary napkins, diapers, bandages, tampons, and the like.

24 Claims, 1 Drawing Sheet

MULTILAYERED APERTURED FILM WRAPPING ELEMENT FOR ABSORBENT ARTICLES

CROSS REFERENCE TO RELATED APPLICATIONS

This invention is related to the following copending applications: U.S. Ser. No. 09/343,759, filed Jun. 30, 1999, entitled "Continuous Method of Providing Individual Sheets from a Continuous Web"; U.S. Ser. No. 09/345,088, filed Jun. 30, 1999, entitled "Tampon with Cover and Nonionic Surfactant"; U.S. Ser. No. 09/345,089, filed Jun. 30, 1999, entitled "Heterogeneous Apertured Film Wrapping Element for Absorbent Articles"; U.S. Ser. No. 09/343,760, filed Jun. 30, 1999, entitled "Domed Tampon with Surfactant-Treated Cover"; U.S. Ser. No. 60/141,688, filed Jun. 30, 1999, entitled "Sealing Roller and Sealing Roller Element, Particularly for Producing a Tampon for Feminine Hygiene and Method Therefore"; and U.S. Ser. No. 60/141,690, filed Jun. 30, 1999, entitled "Tampon for Feminine Hygiene and Process and Apparatus for its Production".

BACKGROUND OF THE INVENTION

The present invention relates to a multilayered apertured film wrapping element for an absorbent article. At least one outer layer of the fluid-impervious plastic material has a continuous phase of a thermoplastic polymeric component and an immiscible, dispersed phase of a thermoplastic polymeric component having a lower melting point. The wrapping element is useful in applications involving heat sealing and similar thermal processes in absorbent articles, such as sanitary napkins, diapers, bandages, tampons, and the like.

There are several types of wrapping elements, including covers, that have been or are currently in use for absorbent articles: woven fabrics, nonwoven fabrics, apertured films, reticulated films, polymer nets, and the like. There has been a progression from woven fabrics to nonwoven fabrics and apertured films in these covers. These covers are often adhesively attached to other components in the absorbent article. An adhesive may be applied as a separate component between the cover and another component, or adhesion may result from "heat sealing" or heating one of the components to cause it to become adhesive.

Nonwoven fabrics may incorporate multicomponent fibers having at least two different melting points. Then these fabrics may be adhered to an absorbent article, such as a tampon, as described in Friese, U.S. Pat. Nos. 4,816,100; 4,836,450; and 4,859,273. This is one example of heat sealing a wrapping element or cover.

It may also be desirable to heat seal an apertured film. While it may be possible to heat seal an apertured film that is formed of only one component, this is generally only in areas where it is acceptable or even desirable that the apertures in the film become closed. However, heat sealing an apertured film to an underlying fibrous structure in a manner that maintains open apertures in the heat sealing area is more complex, and it generally requires the use of a film material having at least two different components having at least two different melting point temperatures. An example of this is described in Thompson et al., U.S. Pat. No. 5,342,334. In this example, the apertured film is formed from a co-extruded film having a higher melting point polymeric material on a first, non-bonded surface, and a lower melting point polymeric material on a second, heat-bondable surface. Unfortunately, this arrangement provides a large surface area of bondable material on the second surface, and it may allow unwanted or overly aggressive adhesion in the manufacturing process or final product. The film may adhere to process equipment, such as the apertured film forming surfaces and heat sealing elements. In addition, both layers of the film are exposed to process equipment.

Therefore, what is needed is an apertured film that is heat sealable in a controlled manner, that maintains open apertures, that separates at least one intermediate layer of the film from process equipment to protect both the layer and the equipment from damage, and that allows improved balance of film properties over a monolayer or bilayer film.

SUMMARY OF THE INVENTION

The present invention relates to a wrapping element useful in absorbent articles. The wrapping element is formed of a fluid-impervious plastic material in the form of a resilient three-dimensional web exhibiting a fiber-like appearance and tactile impression. The fluid-impervious plastic material is formed of a laminate having at least three layers: a first layer, forming a first outer surface of the laminate; a second layer forming a second outer surface of the laminate, opposite the first outer surface; and at least one intermediate layer, disposed between the first and second layers. The first layer has a blend of at least two thermoplastic polymeric components, a continuous phase of a first thermoplastic polymeric component that exhibits a first melting point temperature and a dispersed phase of an immiscible, second thermoplastic polymeric component that exhibits a second melting point temperature, less than the first melting point temperature. Therefore, that when the web is heated to a temperature between the first melting point temperature and the second melting point temperature, the second thermoplastic polymeric component is capable of forming an adhesive bond. The web has first and second surfaces. The first surface is defined at least in part by the either of the first and second layers, and it has a multiplicity of apertures therein. The apertures are defined by a multiplicity of intersecting fiber-like elements interconnected to one another substantially in the plane of the first surface. Each of the fiber-like elements exhibits a cross-section having a base portion in the plane of the first surface and a sidewall portion joined to each edge of the base portion. The sidewall portions extend generally in the direction of the second surface of the web, and the intersecting sidewall portions are interconnected to one another intermediate the first and the second surfaces of the web. The interconnected sidewall portions terminate substantially concurrently with one another in the plane of the second surface. In another aspect, the invention relates to a tampon having an absorbent structure substantially enclosed by the wrapping element.

The invention also relates to a method of forming a wrapping element useful in absorbent articles. The method includes the steps of forming a laminate having at least three layers, applying fluid at a temperature greater than ambient temperature to the laminate while it is supported on a three-dimensional surface to form a resilient three-dimensional web, and separating the web into individual pieces of material of a size appropriate for a wrapping element.

Again, the web has first and second surfaces, and the first surface is defined at least in part by the either of the first and second layers and having a multiplicity of apertures therein. Each of the apertures is defined by a multiplicity of intersecting fiber-like elements interconnected to one another substantially in the plane of the first surface, and each of the fiber-like elements exhibits a cross-section comprising a base portion in the plane of the first surface and a sidewall portion joined to each edge of the base portion. The sidewall portions extend generally in the direction of the second surface of the web, and the intersecting sidewall portions are interconnected to one another intermediate the first and the second surfaces of the web. The interconnected sidewall portions terminate substantially concurrently with one another in the plane of the second surface. The laminate is substantially as described above.

Finally, the invention also relates to a method of making a tampon. The method includes separating a cover from a supply of a resilient three-dimensional web such as that described above, substantially enclosing an absorbent structure with the cover, and applying thermal energy to the cover to heat it to a temperature between the first melting point temperature and the second melting point temperature of the first layer to form an adhesive bond.

DETAILED DESCRIPTION OF THE PREFERRED EMBODIMENT

Figure 1:
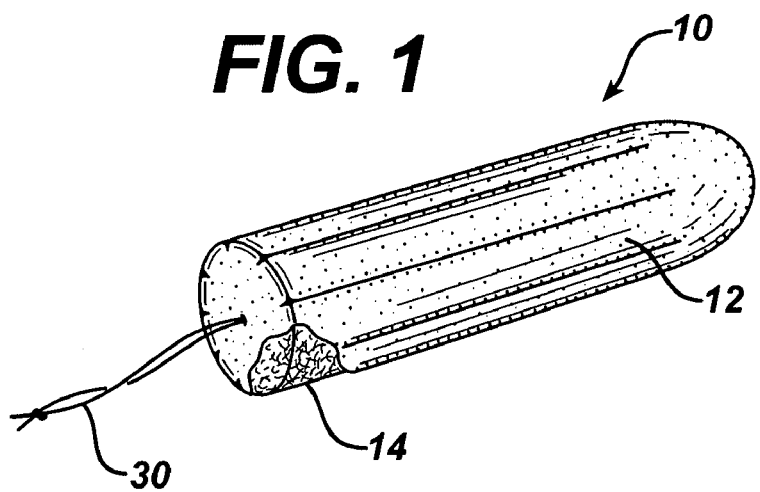
FIG. 1 is a tampon having an apertured film cover according to the present invention.

As used herein, the term "absorbent article" refers to devices that absorb and contain body exudates and that are worn on or inside the body. These devices preferably absorb and contain blood, urine, and/or vaginal discharges, such as bandages, dental and nasal tampons, diapers, sanitary napkins, incontinence guards or pads, interlabial sanitary protection devices, and internal sanitary protection devices such as tampons.

As used herein, the term "apertured film" refers to a fluid-impervious plastic material in the form of a resilient three-dimensional web having first and second surfaces and exhibiting a fiber-like appearance and tactile impression. The first surface of the three-dimensional web has a multiplicity of apertures therein. Preferably, each of the apertures is defined by a multiplicity of intersecting, fiber-like elements interconnected to one another substantially in the plane of the first surface. Each of the fiber-like elements exhibits a cross-section, preferably having a base portion in the plane of the first surface and a sidewall joined to each edge of the base portion. The sidewall portions extend generally in the direction of the second surface of the three-dimensional web. Further, the intersecting sidewall portions are interconnected to one another intermediate the first and second surfaces of the web. The interconnected sidewall portions preferably terminate substantially concurrently with one another in the plane of the second surface.

As used herein, the term "wrapping element" refers to an element of an absorbent article that, alone or in conjunction with one or more additional element(s), substantially encloses an absorbent structure. As used herein, the term "cover" refers to a wrapping element located on the outer surface of an absorbent article.

The absorbent articles of the present invention, e.g., a tampon 10, comprise an apertured film wrapping element, e.g., a cover 12, and an absorbent structure 14. The wrapping element at least partially encloses the absorbent structure that is generally designed and constructed to absorb and contain bodily exudates As indicated above, the presence of the sidewalls 16 between the first surface 18 and second surface 20 of the web imparts a generally three-dimensional quality to the wrapping element. This three-dimensional quality is distinct from the generally two-dimensional quality of a reticulated film, such as that described in U.S. Pat. No. 4,710,186, the disclosure of which is hereby incorporated by reference. Two-dimensional reticulated films more readily allow portions of the absorbent materials of the absorbent structure to protrude through to the surface of the absorbent article, such as a tampon.

The three-dimensional quality provided by the sidewalls 16 helps to separate the absorbent materials of the absorbent structure 14 from the surface of the absorbent article, often defined by the first surface 18 of the wrapping element 12. The longer the sidewalls 16, the greater the separation of the absorbent structure materials from the article surface and the less likely it is that any absorbent structure materials will protrude through the openings 22 in the apertured film 12 to contact the user's body tissues during use.

Some types of absorbent materials may protrude more easily through the openings 22 in the apertured film 12, and thus, longer sidewalls 16 may be needed to prevent protrusion. It will be recognized by those familiar in the art that tampons 10 are often compressed during the manufacturing process. Such compression may cause the sidewalls 16 of the apertured film 12 to fold over. Such folding, however, does not appear to detract from the ability of the sidewalls 16 to prevent protrusion of the absorbent materials through the openings 22 in the apertured film 12.

Figure 2:
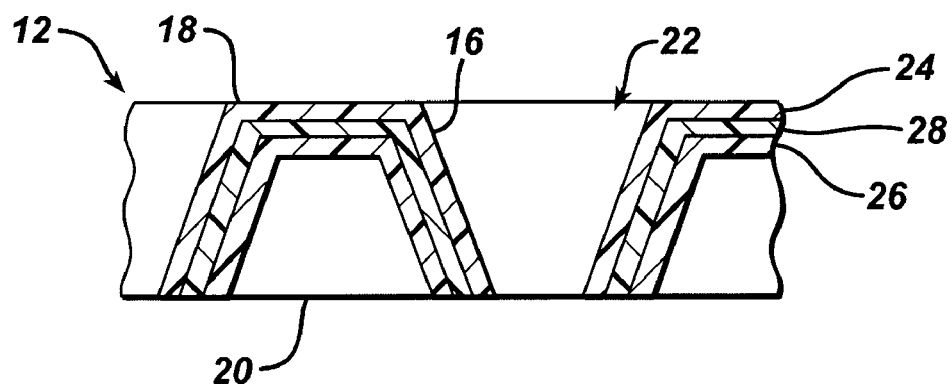
FIG. 2 is an enlarged cross-section of an apertured film according to the present invention.
Figure 3:
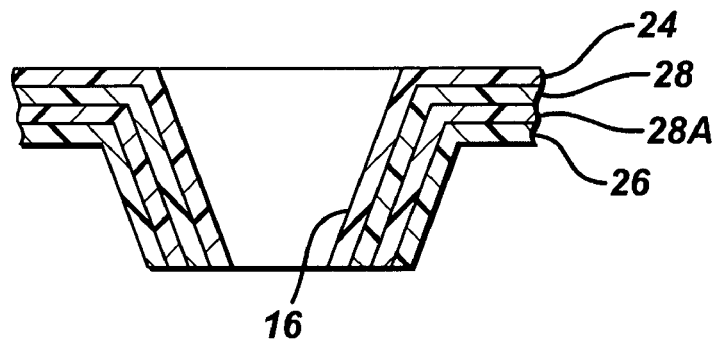
FIG. 3 is an enlarged cross-section of an alternative embodiment of the apertured film of the present invention.

FIG. 2 is an enlarged cross-section of a wrapping element, e.g., cover 12, according to the present invention. The wrapping element is a web having first surface 18 and second surface 20. As can be seen in this figure, the web is preferably comprised of a laminate having a plurality of layers: a first layer 24, a second layer 26, and an intermediate layer 28 disposed therebetween. Although only one intermediate layer 28 is illustrated in this FIG. 2, it will be apparent to one of ordinary skill that additional intermediate layers (e.g., second intermediate layer 28A in FIG. 3) may also be added.

The first layer forms a first outer surface of the laminate. This layer is formed of a blend of at least two thermoplastic polymeric components. The first thermoplastic polymeric component forms a continuous phase that exhibits a first melting point temperature. In order to form the continuous phase, it is preferred that the first thermoplastic polymeric component be present at about 45 to about 95 wt-% of the layer, more preferably about 60 to about 80 wt-% of the layer. A dispersed phase comprises a second thermoplastic polymeric component that exhibits a second melting point temperature. It is preferred that the second thermoplastic polymeric component is present at about 55 to about 5 wt-% of the layer, more preferably about 40 to about 20 wt-% of the layer. In addition, the second melting point temperature is sufficiently less than the first melting point temperature to allow the film to be heated to a temperature between the first and second melting point temperatures, rendering the second thermoplastic polymeric component capable of forming an adhesive bond. This bond may be formed between different portions of the wrapping element, or it may be between the wrapping element and another element of the absorbent article. Preferably, the difference between the first melting point temperature and the second melting point temperature is greater than about 20° C., and more preferably, the difference between the first melting point temperature is greater than about 30° C. Most preferably, the difference is greater than about 40° C.

The continuous phase provides the "backbone" of the layer and contributes most of the layer's mechanical properties, such as tensile strength, stiffness, elongation at break, coefficient of friction, modulus, and the like. The first thermoplastic polymeric component substantially provides these properties. Therefore, the first thermoplastic polymeric component of the first layer will be chosen for its desirable properties. A representative, non-limiting list of suitable polymers for the first thermoplastic polymeric component includes polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. Preferred first thermoplastic polymeric components include polyolefins, especially polypropylene.

The dispersed phase provides localized areas for thermal bonding to adjacent elements. The second thermoplastic polymeric component provides these properties, and it may also contribute to some of the mechanical properties, including coefficient of friction. A representative, non-limiting list of suitable polymers for the second thermoplastic polymeric component includes polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. Preferred second thermoplastic polymeric components include polyethylene and its copolymers, especially linear low density polyethylene (LLDPE), low density polyethylene (LDPE) and EVA.

The first and second thermoplastic polymeric components of the first layer should be selected to allow the desired properties of each material to be apparent. For example, a combination of polypropylene (continuous phase) and polyethylene (dispersed phase) employs thermoplastic polymeric components that have a viable melting point differential to allow for heat sealing and that are compatible, e.g., they can be extruded from the same extrusion head without charring, etc. In contrast, a combination of LLDPE (continuous phase) and LDPE (dispersed phase) would be less desirable, because there is insufficient melting point differential to provide for acceptable heat sealing. Additionally, a combination of nylon-6 (continuous phase) and EVA (dispersed phase) would also be less desirable as the dispersed phase is likely to be degraded in a film extrusion process.

In addition, other components and further additives can be added to the first layer in an amount that will not hinder obtaining the object of the present invention, including, without limitation, antioxidants, UV absorbers, lubricants, antiblock and slip agents, plasticizers, nucleating agents, antistatic agents, flame retardants, pigments, dyes, and inorganic or organic fillers.

The second layer forms a second outer surface of the laminate, opposite the first outer surface. This layer may have fewer restrictions than the first layer.

It may have only one component, or it may also be a blend of at least two components. If a blend is chosen, it may be homogeneous, or it may be a blend of at least two immiscible polymeric materials. A representative, non-limiting list of suitable polymers for the second layer includes polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like; or combinations thereof. However, the second layer may also include other polymers, including a discrete phase comprising thermoset polymers.

In addition, other components and further additives can be added to the second layer in an amount that will not hinder obtaining the object of the present invention, including, without limitation, antioxidants, UV absorbers, lubricants, antiblock and slip agents, plasticizers, nucleating agents, antistatic agents, flame retardants, pigments, dyes, and inorganic or organic fillers.

In a preferred embodiment, the second layer of the wrapping element has the characteristics described above for the first layer. It may be the same as or different than the first layer. Preferably, the first and second layers are substantially identical to enable a single extruder to form both layers.

At least one intermediate layer is disposed between the first and second layers to contribute additional, desirable properties to the wrapping element. For example, the at least one intermediate layer (otherwise described as "intermediate layer(s)") may have an elevated loading of pigment to increase the opacity of the wrapping element. If pigments are loaded in a monolayered film at levels that are too high, the additives may "plate out" of the film, creating poorer appearance and clogging and/or abrading processing equipment. However, elevated loading of pigments in an intermediate layer is less likely to cause the same extent of the problems likely caused if this loading exists in an outer layer or monolayer. Therefore, it is possible to have pigment loading in excess of 10 wt-% in the intermediate layer, preferably, about 1 to about 10 wt-%, and most preferably, about 8 to about 10 wt-% pigment in the intermediate layer. This pigment loading, in combination with some pigment loading in the first and/or second layers may result in films having a pigment loading in excess of about 5 wt-%, preferably, about 5 to about 8 wt-%, and most preferably, an overall pigment loading in the film of about 6 to about 7 wt-%.

In addition, the intermediate layer(s) may comprise polymeric materials that are softer, tackier, more ductile, and have a lower modulus, etc., than the materials in the outer two layers. This can result in a wrapping element that has improved softness and drape. In contrast, using the same polymeric materials in a monolayer film may increase the likelihood that the film will stick to process equipment surfaces or to itself, may increase the tackiness of the film, or may cause the film to be too limp. It may also reduce the ability of the film to form the desired apertures.

Further, the intermediate layer(s) may comprise polymeric materials that are stiffer, than the materials in the outer two layers. This can result in a more defined apertured web that better maintains its three-dimensional characteristics. Again, using these polymeric materials in a monolayer film may reduce the tendency of the aperturing process to form desirable apertures. Other useful variations in the intermediate layer(s) will be apparent to those of ordinary skill in the art.

The intermediate layer(s) may be formed of a single thermoplastic polymeric material, or it may be formed of at least one blend of at least two immiscible polymeric materials. A representative, non-limiting list of polymeric materials that may be used in the intermediate layer(s) includes polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. Preferred intermediate layer polymeric materials include polyolefins, especially polypropylene, and ethylene copolymers, especially EVA.

If the intermediate layer(s) is formed of a blend, it is preferred that the first thermoplastic polymeric component of the intermediate layer(s) represents about 45 to about 99 wt-% of the film and forms a continuous phase. One or more additional polymeric materials of the intermediate layer(s) may then form one or more dispersed phase within the continuous phase. Again, the first and second thermoplastic polymeric components of a blended intermediate layer should be selected to allow the desired properties of each material to be apparent.

Again, other components and further additives can be added to the intermediate layer(s) in an amount that will not hinder obtaining the object of the present invention, including, without limitation, antioxidants, UV absorbers, lubricants, antiblock and slip agents, plasticizers, nucleating agents, antistatic agents, flame retardants, pigments, dyes, and inorganic or organic fillers.

It is also necessary to use care in selecting the appropriate individual layers of the laminate. They should be selected to provide appropriate laminate integrity. This integrity relates to effectiveness during heat sealing, resistance to degradation under processing conditions, etc. For example, the following combinations of laminate layers have been found to be acceptable: Polypropylene/polyethylene (first and second layers) with polyethylene/EVA (intermediate layer) and LLDPE/LDPE (first and second layers) with LDPE/high density polyethylene ("HDPE") (intermediate layer). In contrast, a combination of nylon-6 and HDPE would be less desirable, because the laminate layers are likely to separate.

The absorbent structure may be any absorbent means that is capable of absorbing and/or retaining liquids (e.g., menses and/or urine). The absorbent structure can be manufactured in a wide variety of sizes and shapes and from a wide variety of liquid-absorbing materials. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibers; synthetic materials, such as polyester fibers, polyolefin fibers, absorbent foams, absorbent sponges, superabsorbent polymers, absorbent gelling materials; formed fibers, such as capillary channel fibers and multilimbed fibers; combinations of materials, such as synthetic fibers and wood pulp including coformed fibrous structures (e.g., those materials described in Anderson et al., U.S. Pat. No. 4,100,324); or any equivalent material or combinations of materials, or mixtures of these.

The wrapping element of the present invention can be manufactured by standard processes known to those of ordinary skill in the art. For example, the base film that is to be apertured can be extruded through multiple extruders to form the three-layered co-extruded film. Additional extruder heads may be added to form additional layers in the laminated film. This technology is well known to those of ordinary skill in the art. The base film can then be apertured by any of the known processes. Several examples include hot air aperturing, and water jet aperturing. Examples of these process are disclosed in Curro, U.S. Pat. No. 4,695,422; Turi, U.S. Pat. No. 5,567,376; and Mullane, U.S. Pat. No. 4,741,877. The resulting multilayered apertured film can be coated, for example as described in commonly assigned, co-pending application U.S. Ser. No. 09/345,088, filed Jun. 30, 1999, entitled "Tampon with Cover and Nonionic Surfactant", and/or slit to a desired width for use in manufacturing an absorbent A preferred embodiment of the present invention is a tampon 10 having an apertured film cover 12 substantially enclosing an absorbent structure 14. The cover 12 is useful to contain the absorbent structure materials to reduce, preferably prevent, the likelihood that any significant portion of the absorbent structure 14 will escape from the tampon 10 and remain after the tampon 10 has been removed, e.g., by pulling on the withdrawal string 30. The cover 12 can also protect the tissue in contact with the tampon 10 from excessive friction or other irritation during insertion, use, and removal of the tampon 10. Further, the cover 12 can add aesthetic qualities to the tampon 10. Therefore, it is desirable that the cover 12 have the following properties low coefficient of friction, smooth surface, high opacity, clear apertures, and unmelted appearance.

In addition, because the cover 12 contains the absorbent structure 14, and because it is often desirable that the cover 12 and absorbent structure 14 be secured to each other, the cover 12 should be capable of thermally bonding at least to itself in a manner that secures the absorbent structure 14 within it. Preferably, the cover 12 is also capable of thermally bonding to the outer portions of the absorbent structure 14, itself. These thermal bonding processes One method of applying the apertured film cover material to an absorbent structure in the manufacture of a tampon is the use of a cut-and-place unit to cut the material from the slit roll and to place it on the absorbent structure. Another method is generally described in Friese, U.S. Pat. No. 4,816,100, the disclosure of which is herein incorporated by reference. While this describes the use of a nonwoven cover to a tampon, improvements necessary to achieve this are described in the commonly-assigned, copending application, U.S. Ser. No. 09/343,759, filed Jun. 30, 1999, entitled "Continuous Method of Providing Individual Sheets from a Continuous Web", the disclosure of which is herein incorporated by reference. This copending application discloses a method to achieve the total separation of a section of material comprises the following steps: severing a supply material in a plurality of discrete regions along a transverse axis, scoring the material residing between the severed regions along the same transverse axis, and then applying a force sufficient to fracture the scored regions, thereby separating the section of material from its supply.

It is in the latter process that the present invention is particularly useful. In this process, an intermediate layer comprising a relatively low modulus or low ductility material can reduce uncontrolled movement of the cover material as it is perforated, scored, and stretched to form a separated segment of cover material. Particularly desirable cover material that is useful in such a process is one that incorporates a low modulus polymeric material in the intermediate layer(s). A representative, non-limiting list of such materials includes ethylene copolymers, such as ethylene-vinyl acetate ("EVA"), ethylene-propylene, ethylene-ethyl acrylate, and ethylene-acrylic acid; and the like.

EXAMPLE

Two polymeric blends were coextruded through multiple extruders. The two melt streams entered a feed block that split the outside layer polymer blend into two streams, leaving the intermediate layer intact. The outer layers thus enclosed or "sandwiched" the intermediate layer to produce an A-B-A film. 50 wt-% of the film was an immiscible blend of polypropylene and low density polyethylene ("LDPE") evenly distributed in the two A layers, and 50 wt-% of the film was an immiscible blend of linear low density polyethylene ("LL-DPE") and ethylene-vinyl acetate copolymer (8 wt-% vinyl acetate) in the intermediate B layer. The A layers were both of 70 wt-% of the polypropylene in the continuous phase and 30 wt-% of the LDPE in the dispersed phase. This film was provided as P18-3964 by Clopay Plastic Products Company, Inc., of Cincinnati, Ohio, USA, and it had an average basis weight of 20 gsm, a nominal thickness of 8 mils (0.2 mm), and a titanium dioxide pigment loading of about 6.5 wt-%.

The A-B-A film was then apertured by applying jets of hot air and vacuum at about 33° C. while being supported by a cylindrical forming surface substantially as described in James et al., U.S. Pat. No. 5,916,462, and Zimmerli, U.S. Pat. No. 3,054,148. The differences between the disclosures therein and the process used herein would not be expected to change the results described hereinbelow. The resulting apertured film had a repeating pattern of substantially uniform, round apertures having a diameter of about 0.62 mm, an open area of about 26%, and an equivalent hydraulic diameter ("EHD"), as measured by the formula EHD=4* area/perimeter, of about 26 mils (0.65 mm).

Open area may be determined by using image analysis to measure the relative percentages of apertured and unapertured, or land, areas. Essentially image analysis converts an optical image from a light microscope into an electronic signal suitable for processing. An electronic beam scans the image, line-by-line. As each line is scanned, an output signal changes according to illumination. White areas produce a relatively high voltage and black areas a relatively low voltage. An image of the apertured formed film is produced and, in that image, the holes are white, while the solid areas of thermoplastic material are at various levels of gray.

The more dense the solid area, the darker the gray area produced. Each line of the image that is measured is divided into sampling points or pixels. The following equipment can be used to carry out the analysis described above: a Quantimet Q520 Image Analyzer (with v. 5.02B software and Grey Store Option), sold by LEICA/Cambridge Instruments Ltd., in conjunction with an Olympus SZH Microscope with a transmitted light base, a plan 1.0× objective, and a 2.50× eyepiece. The image can be produced with a DAGE MTI CCD72 video camera.

A representative piece of each material to be analyzed is placed on the microscope stage and sharply imaged on the video screen at a microscope zoom setting of 10×. the open area is determined from field measurements of representative areas. The Quantimet program output reports mean value and standard deviation for each sample.

EHD was measured according to the procedure disclosed in Turi et al., U.S. Pat. No. 5,567,376. However, the image was acquired using a ScanJet 4c scanner from Hewlett-Packard, Palo Alto, Calif., USA, and analyzed using Image-Pro software from Media Cybernetics, Silver Springs, Md., USA. These changes do not significantly alter any results.

The apertured film was coated with Polysorbate 20 (TWEEN 20, available from ICI, Atlas Chemical Division, of Wilmington, Del., USA, by applying a fine spray of a solution formed of 1 part TWEEN 20 dissolved in 2 parts (v/v) isopropyl alcohol, and it was slit to a width of about 47 mm. TWEEN 20 was applied to the film substrate at ambient temperature of about 2° C. with a target coating weight of about 1 wt-%. The coating weight is measured based upon the TWEEN 20 as the alcohol solvent volatilizes. This is described in greater detail in commonly assigned, co-pending application U.S. Ser. No. 09/345,088, filed Jun. 30, 1999, entitled "Tampon with Cover and Nonionic Surfactant".

The slit film was cut to form a cover having a length of about 125 mm. The cover is applied to an absorbent web comprising 75 wt-% rayon and 25 wt-% cotton having a length of about 235 mm, a width of about 50 mm and a target weight of about 2.7 g. The cover was heat sealed to one end of the absorbent web in a manner generally described in U.S. Ser. No. 60/141,688, filed Jun. 30, 1999, entitled "Sealing Roller and Sealing Roller Element, Particularly for Producing a Tampon for Feminine Hygiene and Method Therefore", and copending application U.S. Ser. No. 09/343,759, filed Jun. 30, 1999, entitled "Continuous Method of Providing Individual Sheets from a Continuous Web". The covered web was then compressed in a tampon press, as generally described in Friese et al., U.S. Ser. No. 07/596,454, filed Oct. 12, 1990, and EP-B-0 422 660. The resulting tampons had a weight of between 2.55 and 3.2 g. During processing of this film, it was noted that the cover was heat-sealable without blocking the apertures and without melting them through, and that the heat-sealable apertured film did not adhere to the aperturing drum.

The disclosures of all US patents and patent applications, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A tampon comprising an absorbent structure substantially enclosed by a cover wherein (1) the cover comprises fluid-impervious plastic material in the form of a resilient three-dimensional web exhibiting a fiber-like appearance and tactile impression, (2) the fluid-impervious plastic material comprises a laminate having at least three layers:

a first outer layer comprising a blend of at least two thermoplastic polymeric components, a continuous phase of a first thermoplastic polymeric component that exhibits a first melting point temperature and a dispersed phase of an immiscible, second thermoplastic polymeric component that exhibits a second melting point temperature, less than the first melting point temperature, such that when the web is heated to a temperature between the first melting point temperature and the second melting point temperature, the second thermoplastic polymeric component is capable of forming an adhesive bond;

a second outer layer, opposite the first outer layer; and at least one intermediate layer, disposed between the first and second outer layers; and (3) the web has first and second surfaces, the first surface defining a plane having a multiplicity of apertures therein and being defined at least in part by one of the first and second layers, each of the apertures being defined by a multiplicity of intersecting fiber-like elements interconnected to one another substantially in the plane of the first surface, the web as defined by each of the fiber-like elements exhibiting a cross-section comprising a base portion in the plane of the first surface and a sidewall portion joined to each edge of the base portion, the sidewall portions extending generally in the direction of the second surface of the web, the sidewall portions being interconnected to one another intermediate the first and the second surfaces of the web to form interconnected sidewall portions terminating substantially concurrently with one another in a plane defined by the second surface.

2. The tampon of claim 1 wherein the first thermoplastic polymeric component is selected from the group consisting of polyolefins, polyesters, polyamides, polyurethanes, polystyrenes, halogenated polymers, and copolymers thereof.

3. The tampon of claim 2 wherein the first thermoplastic polymeric component comprises a polyolefin.

4. The tampon of claim 1 wherein the second thermoplastic polymeric component is selected from the group consisting of polyolefins, polyesters, polyamides, polyurethanes, polystyrenes, halogenated polymers, and copolymers thereof.

5. The tampon of claim 4 wherein the second thermoplastic polymeric component comprises a polyolefin.

6. The tampon of claim 1 wherein the difference between the first melting point temperature and the second melting point temperature is greater than about 20° C.

7. The tampon of claim 1 wherein the first layer comprises about 45 to about 95 wt-% of the first thermoplastic polymeric component and about 55 to about 5 wt-% of the second thermoplastic polymeric component.

8. The tampon of claim 1 wherein the second layer comprises a blend of at least two thermoplastic polymeric components, a continuous phase of a first thermoplastic polymeric component that exhibits a first melting point temperature and a dispersed phase of an immiscible, second thermoplastic polymeric component that exhibits a second melting point temperature, less than the first melting point temperature, such that when the web is heated to a temperature between the first melting point temperature and the second melting point temperature, the second thermoplastic polymeric component is capable of forming an adhesive bond.

9. The tampon of claim 8 wherein the first thermoplastic polymeric component of the second layer is selected from the group consisting of polyolefins, polyesters, polyamides, polyurethanes, polystyrenes, halogenated polymers, and copolymers thereof.

10. The tampon of claim 9 wherein the first thermoplastic polymeric of the second layer component comprises a polyolefin.

11. The tampon of claim 8 wherein the second thermoplastic polymeric component of the second layer is selected from the group consisting of polyolefins, polyesters, polyamides, polyurethanes, polystyrenes, halogenated polymers, and copolymers thereof.

12. The tampon of claim 11 wherein the second thermoplastic polymeric component of the second layer comprises a polyolefin.

13. The tampon of claim 8 wherein the difference between the first melting point temperature and the second melting point temperature of the components of the second layer is greater than about 20° C.

14. The tampon of claim 8 wherein the second layer comprises about 45 to about 95 wt-% of the first thermoplastic polymeric component and about 55 to about 5 wt-% of the second thermoplastic polymeric component.

15. The tampon of claim 8 wherein the first and second layers are substantially identical.

16. The tampon of claim 1 wherein the intermediate layer comprises a component selected from the group consisting of polyolefins, polyesters, polyamides, polyurethanes, polystyrenes, halogenated polymers, and copolymers thereof.

17. The tampon of claim 16 wherein the intermediate layer comprises a polyolefin or a polyolefin copolymer.

18. The tampon of claim 17 wherein the intermediate layer comprises a blend of polyethylene and ethylene-vinyl acetate copolymer.

19. The tampon of claim 1 wherein the intermediate layer further comprises one or more components selected from the group consisting of antioxidants, UV absorbers, lubricants, antiblock agents, slip agents, plasticizers, nucleating agents, antistatic agents, flame retardants, pigments, dyes, and fillers.

20. The tampon of claim 19 wherein the intermediate layer comprises greater than about 5 wt-% of a pigment.

21. The tampon of claim 1 wherein the intermediate layer comprises a blend of polymeric materials.

22. The tampon of claim 21 wherein the intermediate layer comprises a blend of about 45 to about 99 wt-% of a first polymeric component and about 1 to about 55 wt-% of a second polymeric component.

23. The tampon of claim 1 which further comprises an additional intermediate layer.

24. A method of making a tampon comprising the steps of:
   separating a cover from a supply of a resilient three-dimensional web exhibiting a fiber-like appearance and tactile impression,
   the web comprising fluid-impervious plastic material which comprises a laminate having at least three layers:
      a first outer layer comprising a blend of at least two thermoplastic polymeric components, a continuous phase of a first thermoplastic polymeric component that exhibits a first melting point temperature and a dispersed phase of an immiscible, second thermoplastic polymeric component that exhibits a second melting point temperature, less than the first melting point temperature, such that when the web is heated to a temperature between the first melting point temperature and the second melting point temperature, the second thermoplastic polymeric component is capable of forming an adhesive bond;
      a second outer layer, opposite the first outer layer, comprising a, blend of at least two thermoplastic polymeric components, a continuous phase of a first thermoplastic polymeric component that exhibits a first melting point temperature and a dispersed phase of an immiscible, second thermoplastic polymeric component that exhibits a second melting point temperature, less than the first melting point temperature, such that when the web is heated to a temperature between the first melting point temperature and the second melting point temperature, the second thermoplastic polymeric component is capable of forming an adhesive bond; and
      at least one intermediate layer, disposed between the first and second outer layers; and
   the web has first and second surfaces, the first surface defining a plane having a multiplicity of apertures therein and being defined at least in part by one of the first and second layers, each of the apertures being defined by a multiplicity of intersecting fiber-like elements interconnected to one another substantially in the plane of the first surface, the web as defined by each of the fiber-like elements exhibiting a cross-section comprising a base portion in the plane of the first surface and a sidewall portion joined the base portion, the sidewall portions extending generally in the direction of the second surface of the web, the sidewall portions being interconnected to one another intermediate the first and the second surfaces of the web to form interconnected sidewall portions terminating substantially concurrently with one another in a plane defined by the second surface;

substantially enclosing an absorbent structure with the cover; and applying thermal energy to the cover to heat it to a temperature between the first melting point temperature and the second melting point temperature of the first layer to form an adhesive bond.

* * * * *